US012257055B1

(12) United States Patent
Taylor et al.

(10) Patent No.: US 12,257,055 B1
(45) Date of Patent: Mar. 25, 2025

(54) SUPERCONDUCTING QUANTUM INTERFERENCE DEVICE (SQUID) ARRAY (SQA) HAVING PREDETERMINED PATTERN ACROSS EACH ROW

(71) Applicant: The United States of America, as represented by the Secretary of the Navy, San Diego, CA (US)

(72) Inventors: Benjamin J. Taylor, Escondido, CA (US); Susan Anne Elizabeth Berggren, San Diego, CA (US); Anna M. Leese de Escobar, Encinitas, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 300 days.

(21) Appl. No.: 18/081,606

(22) Filed: Dec. 14, 2022

(51) Int. Cl.
*G01R 33/24* (2006.01)
*A61B 5/24* (2021.01)
*G01R 33/00* (2006.01)
*G01R 33/035* (2006.01)

(52) U.S. Cl.
CPC ............ *A61B 5/24* (2021.01); *G01R 33/0094* (2013.01); *G01R 33/0354* (2013.01); *A61B 2562/0223* (2013.01); *A61B 2562/043* (2013.01)

(58) Field of Classification Search
CPC .............. A61B 5/24; A61B 2562/0223; G01R 33/0094; G01R 33/0354
See application file for complete search history.

(56) References Cited

U.S. PATENT DOCUMENTS

| | | | |
|---|---|---|---|
| 4,470,023 A | 9/1984 | Lukens | |
| 6,690,162 B1 | 2/2004 | Schopohl | |
| 7,369,093 B2 | 5/2008 | Oppenlander | |
| 8,179,133 B1 | 5/2012 | Kornev | |
| 9,097,751 B1* | 8/2015 | Longhini | ........... G01R 33/0354 |
| 10,847,573 B1 | 11/2020 | Berggren | |
| 11,145,802 B2 | 10/2021 | Lazar | |
| 11,175,355 B2 | 11/2021 | Mitchell | |
| 2012/0157319 A1* | 6/2012 | Tsukamoto | ........ G01R 33/0354 29/599 |
| 2018/0164385 A1* | 6/2018 | Chesca | .............. G01R 33/0354 |

(Continued)

OTHER PUBLICATIONS

Caputo, P., et al. "High-performance magnetic field sensor based on superconducting quantum interference filters." Applied physics letters 85.8 (2004): 1389-1391.

(Continued)

*Primary Examiner* — Alvaro E Fortich
(74) *Attorney, Agent, or Firm* — Naval Information Warfare Center Pacific; Kyle Eppele; Paul C. Oestreich

(57) ABSTRACT

A superconducting quantum interference device (SQUID) array (SQA) includes at least one row each including SQUIDs. The SQUIDs in each row are connected in parallel and include junctions, such as Josephson junctions, shared among the SQUIDs. The SQUIDs have respective inductance parameters and the junctions have respective critical currents. The respective inductance parameters of the SQUIDs and respective critical currents of the junctions both vary in a predetermined pattern across the row. This improves performance including improved linearity and improved sensitivity.

19 Claims, 5 Drawing Sheets

(56) References Cited

U.S. PATENT DOCUMENTS

2021/0018575 A1* 1/2021 Mitchell .............. H10N 60/82

OTHER PUBLICATIONS

Oppenlaender, Joerg, et al. "Superconducting quantum interference filters operated in commercial miniature cryocoolers." IEEE transactions on applied superconductivity 15.2 (2005): 936-939.

Kalabukhov, A. K., et al. "Analysis of the possibility to amplify an RF signal with a superconducting quantum Interference filter." Journal of Communications Technology and Electronics 53.8 (2008): 934-940.

Prokopenko, Georgy V., et al. "DC and RF measurements of serial bi-SQUID arrays." IEEE transactions on applied superconductivity 23.3 (2012): 1400607-1400607.

De Andrade, Marcio C., et al. "Detection of far-field radio-frequency signals by niobium superconducting quantum interference device arrays." IEEE Transactions on Applied Superconductivity 25.5 (2015): 1-5.

Taylor, B. J., et al. "Characterization of large two-dimensional YBa2Cu3O7-δ SQUID arrays." Superconductor Science and Technology 29.8 (2016): 084003.

Berggren, Susan AE "Computational and Mathematical Modeling of Coupled Superconducting Quantum Interference Devices." Claremont Graduate University and San Diego State University 2012.

McCumber, D. E. "Tunneling and Weak-Link Superconductor Phenomena Having Potential Device Applications." Journal of Applied Physics 39.6 (1968): 2503-2508.

Mccumber, D. E. "Effect of ac impedance on dc voltage-current characteristics of superconductor weak-link junctions." Journal of Applied Physics 39.7 (1968): 3113-3118.

Stewart, W. C. "Current-voltage characteristics of Josephson junctions." Applied physics letters 12.8 (1968): 277-280.

Katz, A. S., S. I. Woods, and R. C. Dynes. "Transport properties of high-Tc planar Josephson junctions fabricated by nanolithography and ion implantation." Journal of Applied Physics 87.6 (2000): 2978-2983.

Malnou, M., et al. "High-Tc superconducting Josephson mixers for terahertz heterodyne detection." Journal of Applied Physics 116.7 (2014): 074505.

Oppenlander, J., et al. "Two dimensional superconducting quantum interference filters." IEEE transactions on applied superconductivity 13.2 (2003): 771-774.

Oppenlander, Jorg, et al. "Superconducting multiple loop quantum interferometers." IEEE transactions on applied superconductivity 11.1 (2001): 1271-1274.

Oppenlander, J., Ch Haussler, and N. Schopohl. "Non-Φ0-periodic macroscopic quantum interference in one-dimensional parallel Josephson junction arrays with unconventional grating structure." Physical review B 63.2 (2000): 024511.

Shadrin, A. V., et al. "Fraunhofer regime of operation for superconducting quantum interference filters." Applied Physics Letters 93.26 (2008): 262503.

Kornev, V. K., et al. "Bi-SQUID: a novel linearization method for dc SQUID voltage response." Superconductor Science and Technology 22.11 (2009): 114011.

Berggren, Susan, and Anna Leese de Escobar. "Effects of spread in critical currents for series-and parallel-coupled arrays of SQUIDs and Bi-SQUIDs." IEEE Transactions on Applied Superconductivity 25.3 (2014): 1-4.

Bobyl, A. V., et al. "Relaxation of transport current distribution in a YBaCuO strip studied by magneto-optical imaging." Superconductor Science and Technology 15.1 (2001): 82.

Sugimoto, Akira, Tetsuji Yamaguchi, and Ienari Iguchi. "Supercurrent distribution in high-TC superconducting YBa2Cu3O7—y thin films by scanning superconducting quantum interference device microscopy." Applied Physics Letters 77.19 (2000): 3069-3071.

Shikii, S., et al. "Observation of supercurrent distribution in YBa2Cu3O7—67 thin films using THz radiation excited with femtosecond laser pulses." Applied physics letters 74.9 (1999): 1317-1319.

Mitchell, E. E., et al. "Quantum interference effects in 1D parallel high-Tc SQUID arrays with finite inductance." Superconductor Science and Technology 32.12 (2019): 124002.

Labarias, MAG, Muller, KH and Mitchell, EE. "Modelling the transfer function of two-dimensional SQUID and SQIF arrays with thermal noise." Phys. Rev. Applied 17, 064009 (2022).

Müller, K-H., and E. E. Mitchell. "Theoretical model for parallel SQUID arrays with fluxoid focusing." Physical Review B 103.5 (2021): 054509.

* cited by examiner

US 12,257,055 B1

SUPERCONDUCTING QUANTUM INTERFERENCE DEVICE (SQUID) ARRAY (SQA) HAVING PREDETERMINED PATTERN ACROSS EACH ROW

FEDERALLY-SPONSORED RESEARCH AND DEVELOPMENT

The United States Government has ownership rights in this invention. Licensing and technical inquiries may be directed to the Office of Research and Technical Applications, Naval Information Warfare Center Pacific, Code 72120, San Diego, CA, 92152; voice (619) 553-5118; NIWC_Pacific_T2@us.navy.mil. Reference Navy Case Number 105831.

BACKGROUND OF THE INVENTION

There is a general need to simultaneously sense electromagnetic signals having very low and very high relative signal strength. This generally requires a signal detector with exceptionally high linearity, which implies an exceptionally wide Spur Free Dynamic Range (SFDR).

SUMMARY

A superconducting quantum interference device (SQUID) array (SQA) includes at least one row each including SQUIDs. The SQUIDs in each row are connected in parallel and include junctions, such as Josephson junctions, shared among the SQUIDs. The SQUIDs have respective inductance parameters and the junctions have respective critical currents. The respective inductance parameters of the SQUIDs and respective critical currents of the junctions both vary in a predetermined pattern across the row. This improves performance including improved linearity and improved sensitivity.

BRIEF DESCRIPTION OF THE DRAWINGS

Throughout the several views, like elements are referenced using like references. The elements in the figures are not drawn to scale and some dimensions are exaggerated for clarity.

DETAILED DESCRIPTION OF EMBODIMENTS

The disclosed systems and methods below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

Various embodiments of the invention provide an enhanced superconducting quantum interference device (SQUID) array (SQA) having improved performance including improved linearity and improved sensitivity. Because SQA have wide detection bandwidths from DC well into GHz frequencies, the SQA with improved linearity and improved sensitivity enables a single small platform that achieves simultaneous detection of many electromagnetic signals having a wide range of relative signal strengths over a wide bandwidth. The disclosed SQA have improved linearity, dV/dB, expected to provide at least ten decibels of improved performance. The disclosed SQA are expected to have magnetic field sensitivity increased by a factor of three to eight for those SQA having more than about ten parallel Josephson junctions in each row. In particular, the disclosed SQA increase the number of efficiently utilized Josephson junctions in each row to more than twenty, while maintaining the improved linearity, dV/dB.

Figure 1:
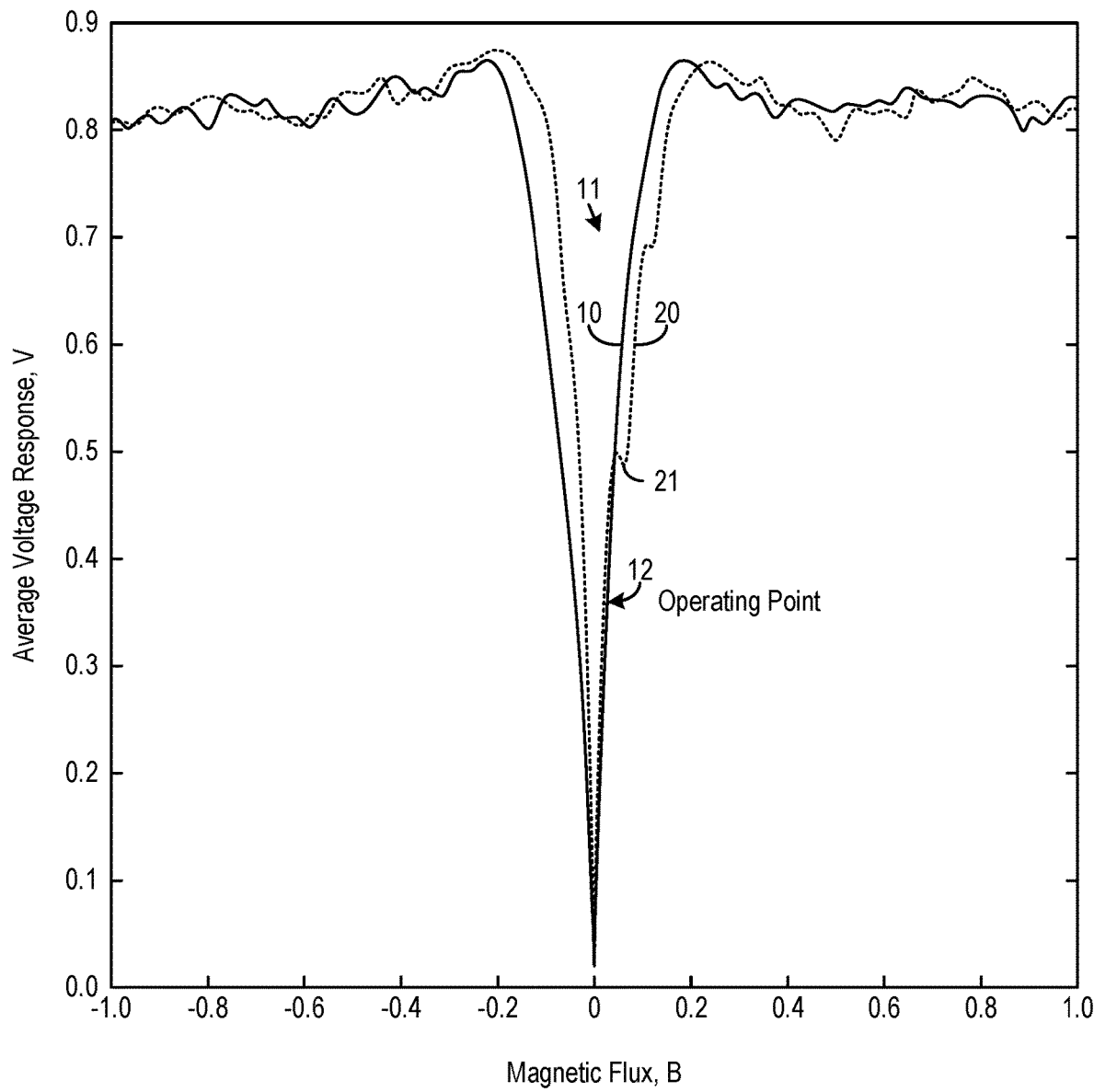
FIG. 1 shows a graph for average voltage response of an example of a superconducting quantum interference device (SQUID) array (SQA) in accordance with an embodiment of the invention.

FIG. 1 shows a graph for average voltage response of an example of a superconducting quantum interference device (SQUID) array (SQA) in accordance with an embodiment of the invention. The example curve 10 of the transfer characteristic V(B) of the SQA includes a prominent so-called anti-peak 11. Because the slope dV/dB is high at the example operating point 12 near the middle of a side of the anti-peak 11, small changes in the magnetic flux through the SQA produce large changes in the voltage generated across the SQA. This makes the SQA a sensitive detector of magnetic fields, including detecting the oscillating magnetic field of electromagnetic radiation well into GHz frequencies. The deficient example curve 20 of a poorly designed SQA is discussed below following disclosure of various embodiments of the invention that avoid such deficiency.

Figure 2:
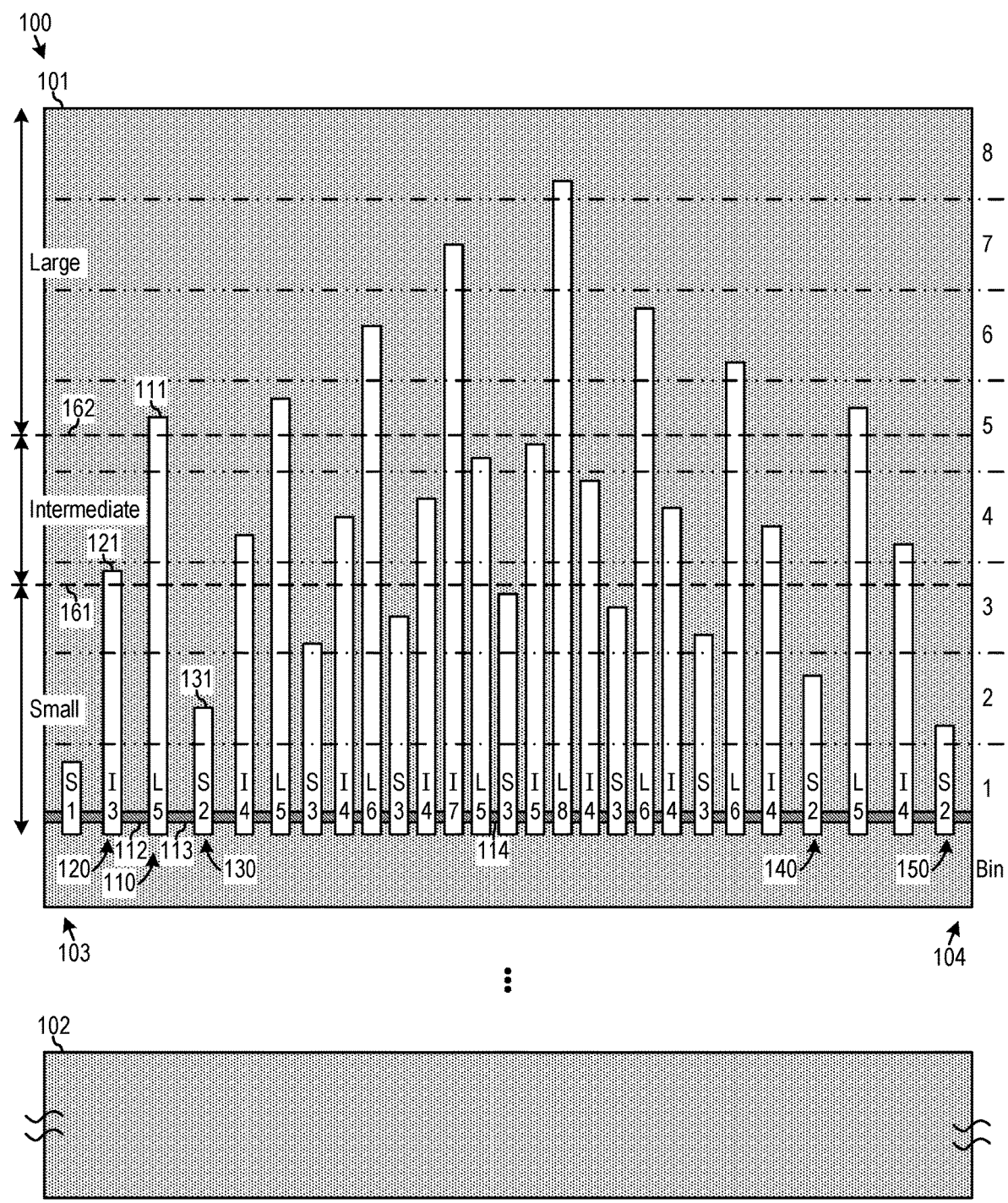
FIG. 2 shows a plan view of a superconducting quantum interference device (SQUID) array (SQA) in accordance with an embodiment of the invention.

FIG. 2 shows a plan view of a superconducting quantum interference device (SQUID) array (SQA) 100 in accordance with an embodiment of the invention. The top row 101 of the SQA 100 is a thin rectangular layer of superconducting material incorporating twenty-seven SQUIDs. Each of the SQUIDs includes a loop of the superconducting material enclosing an area that is a window in the superconducting material. For example, SQUID 110 includes a loop of the superconducting material surrounding the enclosed area 111. In this embodiment, each of the SQUIDs also includes two junctions disposed on the SQUID's loop of the superconducting material. For example, SQUID 110 includes two junctions 112 and 113 disposed on the loop of the superconducting material surrounding the enclosed area 111. In other embodiments, each SQUID in the SQA has only one junction or more than two junctions.

In one embodiment, the superconducting material is a high-temperature cuprate-based superconductor $YBa_2Cu_3O_x$ having $6.3 \leq x \leq 7$. In other embodiments, the superconducting material has formula $R_{1-y}M_yBa_2Cu_{3-z}T_zO_x$, where oxygen content is $6.3 \leq x \leq 7$, $0 \leq y \leq 1$, $0 \leq z \leq 1$, R is calcium or one or more rare earths, M is calcium if absent from R or one or more rare earths not included in R, and T is at least one of cobalt (Co), iron (Fe), nickel (Ni), or zinc (Zn).

In the embodiment of FIG. 2, the quantum interference device (SQUID) array (SQA) 100 includes rows 101 through 102 connected in series. Each row 101 or 102 includes n=27 SQUIDs that are connected in parallel. Each row 101 or 102 also includes n+1 junctions shared among the n SQUIDs. Each of the n SQUIDs includes two of the n+1 junctions, and each of the n SQUIDs, besides an outermost two of the n SQUIDs in row 101 or 102, share their two of the n+1 junctions with adjacent ones of the n SQUIDs. For example, SQUID 110 includes two junctions 112 and 113, with junction 112 shared with adjacent SQUID 120 enclosing area 121 and junction 113 shared with adjacent SQUID 130 enclosing area 131.

To improve performance of the SQA 100, and especially to improve linearity of the SQA 100 at the operating point, respective inductance parameters of the SQUIDs and respective critical currents of the junctions both vary in a predetermined pattern across the row 101 as discussed below.

In one embodiment, the junctions including junctions 112 and 113 are Josephson junctions. A Josephson junction is a region of material that provides a weak link between two fully superconducting regions through which paired superconducting electrons can tunnel via a quantum mechanical process. The critical current of a Josephson junction is the transition point where normal-state (unpaired) electrons also begin to tunnel through so then the Josephson junction transitions from purely superconducting to a non-linear resistive behavior. In an embodiment having ion-damage Josephson junctions, the critical currents of the Josephson junctions are proportional to their varying widths because their remaining dimensions and other characteristics are all the same. For example, the critical current of junction 112 near an outer end 103 of row 101 is about three times the critical current of junction 114 near the middle of row 101 because the width of junction 112 is about three times the width of junction 114. In another embodiment having step-edge Josephson junctions, the critical currents do not follow a strictly linear dependence on the width of the junctions; however, this behavior can also be accounted for when determining the width distribution to use across the parallel SQA segment.

The respective inductance parameters, $\beta_L$, of the SQUIDs in each row 101 or 102 vary over at least an order of magnitude. Each inductance parameter is $\beta_L = 2LI_0/\Phi_0$ where L is the loop inductance of each SQUID, $I_0$ is the critical current of each junction, and $\Phi_0$ is the flux quantum. Note that the inductance parameter is sometimes alternatively defined in the related art to include an extra factor of $\pi$ not included in the above equation. The loop inductance of each SQUID is a sum of a geometric inductance around the respective enclosed area of the SQUID and a typically smaller kinetic inductance from the layer of superconducting material surrounding the respective enclosed area of the SQUID.

The geometric inductance around the respective enclosed area of each SQUID is calculated, for example, from a flat wire inductance formula applied to each of the two sides and the two ends surrounding the respective enclosed area. From this formula, the geometric inductance of each side of a SQUID is $L_g = 0.2\ell\{\ln[2\ell/(w+t)] + 0.5 + 0.2235(w+t)/\ell\}$ where $L_g$ is the geometric inductance of the side in pH and $\ell$, w, and t are the length, width, and thickness of the side in mm. From the flat wire inductance formula, the geometric inductances around the SQUIDs are approximately proportional to the length of the perimeters of their varying enclosed areas. In FIG. 2, the length of the perimeters of the enclosed areas of the SQUIDs and hence their geometric inductances are approximately proportional to their varying heights because their identical widths are comparatively insignificant. In other embodiments, both the widths and the heights vary for the enclosed areas.

The kinetic inductance of the layer of superconducting material surrounding the respective enclosed area of each SQUID is calculated from the kinetic inductance per square applied to each of the two sides and the two ends surrounding the respective enclosed area. The kinetic inductance for each side of the SQUID is the number of squares, which is the length $\ell$ of the side divided by the width w of the side, times the kinetic inductance per square. The kinetic inductance per square of the superconducting material is $L_k = (\mu_0 \lambda_0^2)/\{t[1-(T/T_c)^P]\}$ where T is the temperature and the superconductor is characterized by empirical parameters including the penetration depth at absolute zero $\lambda_0$, the critical temperature $T_c$, and $1.94 \leq P \leq 3.36$. To avoid over counting, the kinetic inductance of each shared side should be divided by two, with half assigned to each adjacent SQUID. The junctions themselves have kinetic inductance that can be accounted for, but these are relatively insignificant and hence typically neglected.

However, for illustrative purposes only in FIG. 2, all kinetic inductances are disregarded, so the respective inductance parameters of the SQUIDs can become depicted as proportional to the varying heights of their enclosed areas.

The respective inductance parameters, $\beta_L$, of the SQUIDs in each row 101 or 102 vary over at least an order of magnitude according to a distribution of a predetermined pattern. Example distributions include Gaussian and weighted Gaussian distributions. In an embodiment, the inductance parameters range over an order of magnitude $\alpha/10 \leq \beta_L \leq \alpha$ with $0.1 < \alpha < 10$. To achieve good linearity at the operating point as discussed below, a typical value is $\alpha \approx 1$ so that the average value over all the inductance parameters becomes $1/\pi$.

In summary, the respective inductance parameters of the SQUIDs and the respective critical currents of the junctions both vary in a predetermined pattern across the row 101 to improve performance of the SQA 100. The respective inductance parameters of the SQUIDs including SQUIDS 120, 110, and 130 are illustrated as proportional to their varying heights shown in FIG. 2 and the respective critical currents of the junctions including junctions 112, 113, and 114 are illustrated as proportional to their varying widths shown in FIG. 2.

Figure 3:
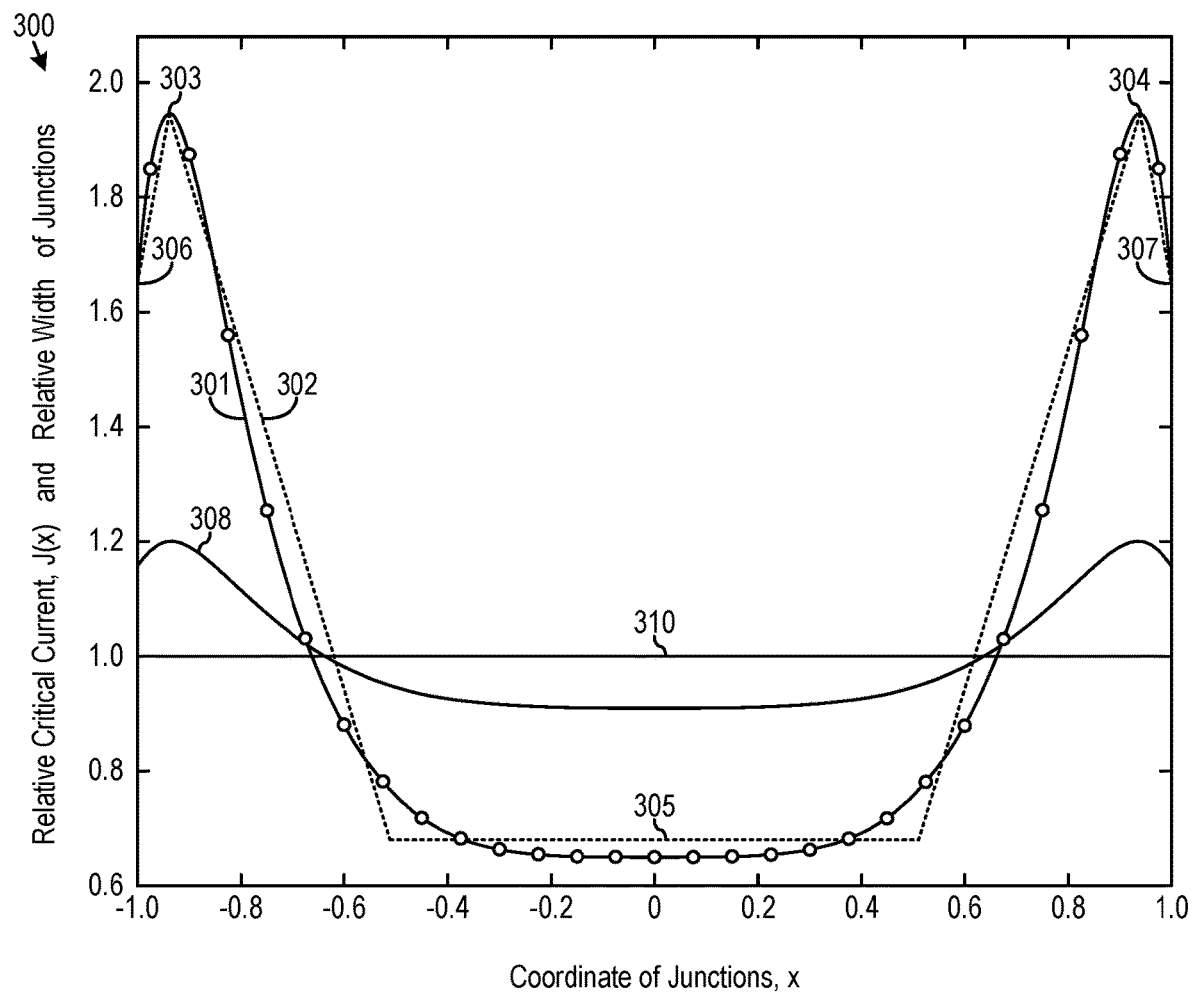
FIG. 3 shows a graph for critical currents and corresponding widths of the junctions of the top row of SQUIDs in the SQA of FIG. 2.

FIG. 3 shows a graph 300 for critical currents and corresponding widths of the junctions of the top row 101 of SQUIDs in the SQA 100 of FIG. 2. The inventors have discovered a functional relation that describes the manner in which DC bias current passing through the SQA 100 flows primarily toward the edges of the thin rectangular layer of superconducting material of the SQA 100. The functional relation is a power of the following empirical equation:

$$J(x) = a \times \cos h[(bx^2)^c] \times \{0.5 + 0.5 \tan h[d(1-x)]\} \times \{0.5 + 0.5 \tan h[d(1+x)]\} \quad (1)$$

where $-1 \leq x \leq 1$ is a coordinate of the junctions varying across each row from x=-1 at the first end to x=1 at the second end $J(x)$ is the DC bias current through each of the junctions disposed at the coordinate x, and the power>0 and a, b, c, and d are empirical parameters of the functional relation. Curve 301 in graph 300 shows the DC bias current, $J(x)$, expected in a specific example having a power of 1, a=1.5542, b=2.2246, c=1.0513, and d=9.8919.

In FIG. 3, line 310 gives the previously projected DC bias current through the SQA before accounting for the non-uniform current flow (current crowding). Without such current crowding, the DC bias current through the SQA was previously projected to become evenly divided between the SQUIDs in the SQA. With such even dividing of the DC bias current, all of the SQUIDs were previously designed with identical junctions having the same critical current where their junctions cease being purely superconductive and begin becoming resistive. Thus, the scale of the vertical axis of graph 300 is normalized to the critical current of the identical junctions of the SQUIDs in the SQA assuming the DC bias current through the SQA is evenly divided between the SQUIDs. Thus, line 310 gives, for previously designed SQA, both the previously projected critical current of the junctions in the SQA and the particular DC bias current through the SQA achieving this previously projected critical current through the junctions in the SQA.

However, the DC bias current through the SQA is not evenly divided between the SQUIDs due to the current crowding. Thus, curve 301 for $J(x)$ in graph 300 shows the crowding of the DC bias current through each of the junctions when the total DC bias current through the entire SQA is set a level previously expected to bias all of the identical junctions at their same critical current. Curve 301 shows that the outer identical junctions are actually biased well above their expected critical current of line 310, but the middle identical junctions are actually biased well below their expected critical current of line 310.

Figure 4:
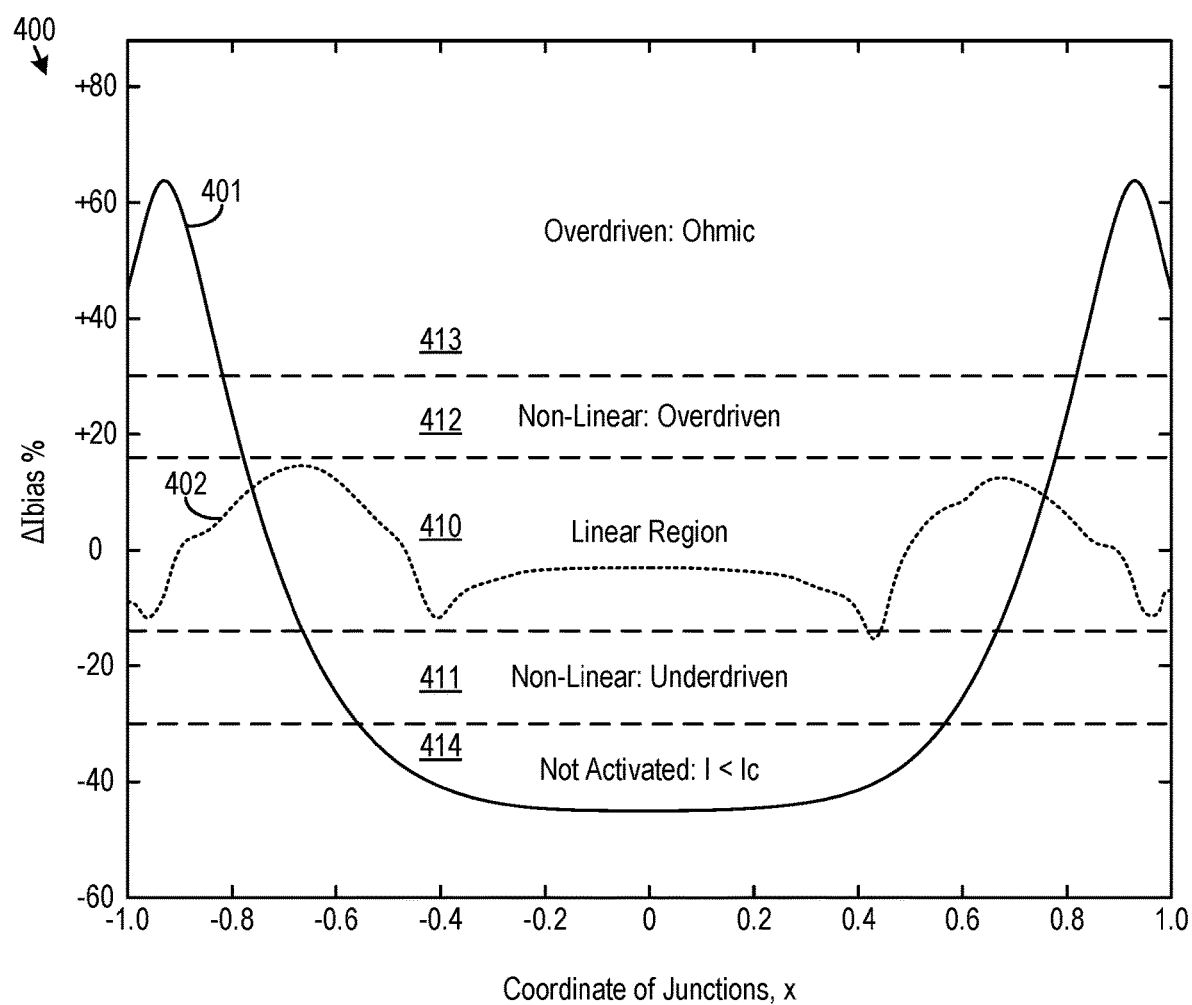
FIG. 4 shows a graph for percent deviation of the bias current through the junctions of the top row of SQUIDs in the SQA of FIG. 2.

FIG. 4 shows a graph 400 for percent deviation of the bias current through the junctions of the top row 101 of SQUIDs in the SQA 100 of FIG. 2. FIG. 4 depicts various regions of operation with respect to the resistive nature of the junctions, i.e., dynamic resistance or purely ohmic resistance. The description of the dynamic resistive regions is with respect to the use of an empirical expression based upon a Gaussian form, valid up to the optimal circuit bias point, in lieu of a standard RCSJ model based expression. Depending upon the percent deviation of the DC bias current of the individual junctions from the selected DC bias current of the operating point for the SQA, each individual junction is driven in the linear 410 region, the underdriven non-linear 411 region, the overdriven non-linear 412 region, the purely ohmic overdriven 413 region, or the nonactivated 414 region. Curve 401 show the percent deviation of the DC bias current through identical junctions erroneously designed assuming the DC bias current through the SQA is evenly divided between the SQUIDs. Curve 401 indicates that about half of the SQUIDs in the middle of the SQA are not activated 414, so they make no contribution to the average voltage response (see FIG. 1) of the SQA. About another quarter of the SQUIDs at the outer ends of the SQA are ohmic overdriven 413 so they load and hence degrade the average voltage response of the SQA. About the remaining quarter of the SQUIDs in the SQA operate in the linear 410 region, the underdriven non-linear 411 region, or the overdriven non-linear 412 region so they positively contribute to the average voltage response of the SQA. Only a small fraction of the SQUIDs operate in the preferable linear 410 region.

The inventors have further discovered that varying the respective critical currents of the junctions of the SQUIDS in the SQA compensates for the crowding of the bias current towards the edges of the thin rectangular layer of superconducting material of the SQA 100. Again, the critical currents of Josephson junctions are proportional to their varying widths when their remaining dimensions and other characteristics remain the same. In the embodiment of FIG. 2, the respective widths of the junctions vary across each of row 101 or 102 for varying the respective critical currents of the junctions. For example, referring to FIG. 3, the desired relative critical current of junctions near the outer end is approximately 1.9 and the desired relative critical current of junctions near the middle is approximately 0.65 for a ratio 1.9/0.65 that equals approximately three, and FIG. 2 shows the critical current of junction 112 near an outer end 103 of row 101 is about three times the critical current of junction 114 near the middle of row 101 because the width of junction 112 is about three times the width of junction 114.

Referring again to FIG. 3, the circles on curve 301 specify optimal values for compensating for current crowding, the optimal values specifying the relative critical currents and corresponding widths of the junctions of the top row 101 of SQUIDs in the SQA 100 of FIG. 2. However, such optimal values might be unachievable, for example, because the patterning technology for defining the widths of the junctions has a minimum allowed step increment upon increasing the widths of the junction. Thus in practice, the curve 301 is approximated with the piecewise linear curve 302 that satisfies the discrete steps in the allowed widths of the junctions. For this piecewise linear curve 302, curve 402 in FIG. 4 shows the resulting percent deviation of the DC bias current through the junctions. Curve 402 in FIG. 4 shows the junctions of the SQA 100 of FIG. 2 operate nearly entirely in the preferred linear 410 region. This contrasts with curve 401 showing only a small fraction of the SQA operate in the preferred linear 410 region when all the junctions have the same width because current crowding is overlooked.

Thus, all of the junctions operate within the optimal (linear) dynamic resistive region at a given bias current of a selected operating point 12 of FIG. 1, despite the given bias current through rows 101 and 102 gathering towards the ends 103 and 104 of each row with the given bias current gathering proportional to the functional relation that is the power of $J(x)$ given in equation (1). Preferably, all of the junctions operate in linear 410 region of FIG. 4 despite the DC bias current gathering towards the ends of each row 101 or 102.

In the embodiment of FIG. 2, the respective critical currents of the junctions vary across each of rows 101 and 102 according to the functional relation of a predetermined pattern. The functional relation is a power of equation (1) for $J(x)$ specified above. In correspondence, the respective widths of the junctions vary across each of rows 101 and 102 for varying the respective critical currents of the junctions according to the functional relation of the predetermined pattern.

The respective critical currents of the junctions vary between a first end 103 and opposite second end 104 of the row 101. In correspondence, the respective widths of the junctions vary between the first end 103 and opposite second end 104 of the row 101. As shown in FIG. 3, the respective critical currents have a maximum 303 and 304 critical current near the first and second ends 103 and 104. The respective critical currents have a minimum 305 critical current between the maximum 303 critical current near the first end 103 and the maximum 304 critical current near the second end 104. In correspondence, the respective widths have a maximum 303 or 304 width near the first and second ends 103 and 104. The respective widths having a minimum 305 width between the maximum 303 width near the first end 103 and the maximum 304 width near the second end 104.

However, measurements of fabricated SQA suggest that current crowding is not as dramatic as indicated with curve 301 of FIG. 3 obtained from simulating a thin and uniform rectangular layer of superconducting material. Instead, the SQUIDs of the SQA 100 partially equalize the current crowding. The respective critical currents of the junctions and their widths still vary according to the functional relation that is the power of $J(x)$ given in equation (1), but the value of the power captures the empirically observed partial equalization of the current crowding. The measurements of fabricated SQA suggest that a value for the power of 0.2 captures the partially equalized the current crowding. Curve 308 in FIG. 3 shows the relative critical currents and corresponding widths of the junctions when the power=0.2.

In FIG. 3, the respective widths of the junctions in a middle of the row 101 plateau at the minimum 305 width, and the respective widths of the junctions outside the middle monotonically increase from the minimum 305 width of the plateau to the maximum 303 or 304 width near the first and second ends 103 and 104. The respective widths of the junctions outside the maximum 303 or 304 width near the first and second ends 103 and 104 monotonically decrease from the maximum 303 width near the first end 103 to an intermediate 306 width at the first end 103 and monotonically decrease from the maximum 304 width near the second end 104 to the intermediate 307 width at the second end 104. The intermediate width 306 or 307 is between the minimum 305 width and the maximum 303 or 304 width.

When the widths of the junctions follow the piecewise linear curve 302, the respective widths of the junctions outside the middle linearly increase from the minimum 305 width of the plateau to the maximum 303 or 304 width near each of the first and second ends 103 and 104. The respective widths of the junctions outside the maximum 303 or 304 width near the first and second ends 103 and 104 linearly decrease from the maximum 303 width near the first end 103 to the intermediate 306 width at the first end 103 and linearly decrease from the maximum 304 width near the second end 104 to the intermediate 307 width at the second end 104.

Matching the respective widths of the junctions of the SQUIDs of the SQA to the DC bias current gathered at the edges of the SQA improves the linearity and sensitivity of the SQA by ensuring that all of the SQUIDs contribute to the average voltage response of the SQA and the SQUIDs are fully or predominately biased within the linear 410 region of FIG. 4. In contrast with the related art, performance contributions from all SQUIDs operating in or near their linear 410 region is achieved even when each row of the SQA contains more than twenty or even hundreds or thousands of SQUIDs. Next is discussed controlling the respective inductance parameters of the SQUIDs and their spatial distribution to further improve the linearity and sensitivity of the SQA.

Figure 5:
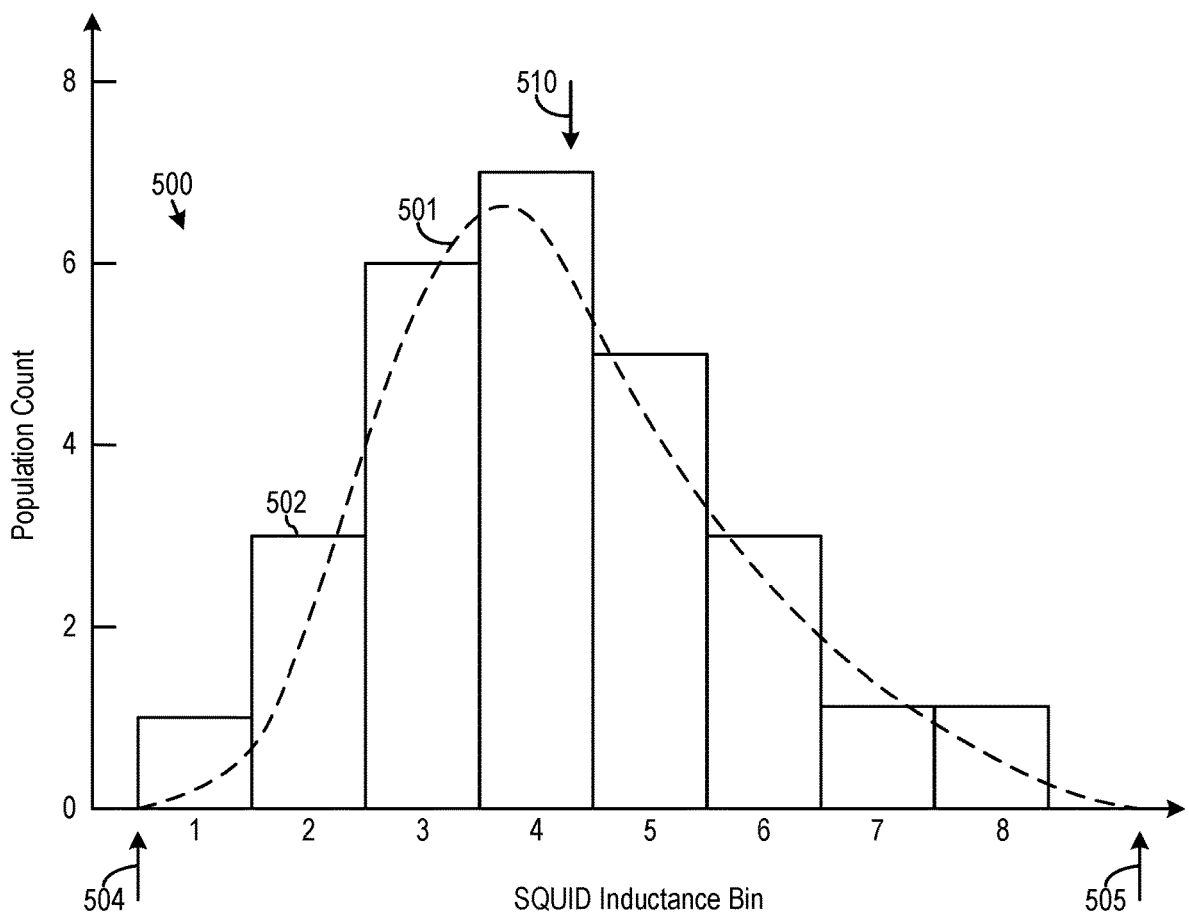
FIG. 5 shows a graph for a Gaussian distribution of a population density over the respective inductance parameters of the top row of SQUIDs in the SQA of FIG. 2.

FIG. 5 shows a graph 500 for a Gaussian distribution 501 of a population density over the respective inductance parameters of the top row 101 of SQUIDs in the SQA 100 of FIG. 2. Recall that for illustrative purposes only in FIG. 2, the respective inductance parameters of the SQUIDs are depicted as proportional to the varying heights of their enclosed areas. For example, the respective inductance parameter of SQUID 110 is depicted as proportional to the height of enclosed area 111. Note that the disregarded kinetic inductances in this simplification for illustrative purposes can be accounted for by reducing the height of each of the enclosed areas by the appropriate amount corresponding to the disregarded kinetic inductances.

The bars in graph 500 specify the population count in each of eight bins for the twenty-seven SQUIDs of FIG. 2. For example, there are three SQUIDs 130, 140, and 150 with respective heights, and hence depicted inductance parameters, falling within the range of bin two, and, therefore, bar 502 in graph 500 has a population count of three for bin two. The Gaussian distribution 501 of a population density for the bars in graph 500 is a skewed Gaussian distribution 501 to account for the definite lower limit 504 on the inductance parameters achieved with the minimum practical enclosed area for the patterning technology, but the upper limit 505 on the achievable inductance parameters is not as physically constrained so long as the inductance parameters in each row vary over at least an order of magnitude.

The number of bins assigned can vary by choice, but typically at least 7 are used, and they are evenly sized. Generally, for a bin scheme extending of a range of $\beta_{L(min)}$ to $\beta_{L(max)}$, with N bins, the bin size will encompass the interval $[b_i-\delta, b_i+\delta]$, where $b_i$ is the center value of the i-th bin given by, $b_i \equiv i(\beta_{L(max)}-\beta_{L(min)})/N$, and $\delta$ is given by, $\delta \equiv b_1-\beta_{min}$. Not all bins must be used, which is often the case for a weighted Gaussian as the larger values are much further away from the mean value of $1/\pi$. For example, we could have $\beta_{L(min)}=0.05$, $\beta_{L(max)}=1.05$, N=10, and the population of bins i=1-10 given by [4, 6, 10, 5, 2, 0, 1, 0, 1, 0]. The average value of the population in each bin is not necessarily the center value $b_i$.

Alternatively, the skewed Gaussian distribution 501 has a unit area under its curve and a random number between zero and one is selected for each of the SQUIDs in row 101 of SQA 100, and the respective inductance parameters for each SQUID is the integration limit for which the area under the curve integrated from the lower limit 504 to this integration limit equals the selected random number. Moreover, in a typical SQA with thousands or tens of thousands of SQUIDS spread over tens or hundreds of rows of the SQA, many discrete steps in the patterning technology's achievable enclosed areas of the SQUIDS have a population count in the hundreds, such that skewed Gaussian distribution 501 results without any binning. Typically, the respective inductance parameters for each SQUID in row 102 are independently selected with respect to position within the row, but the general appearance of row 102 follows the same population distribution as row 101, and with the constraints discussed below.

One condition for good linearity and sensitivity of the SQA 100 is that the average 510 over the inductance parameters, $\beta_L$, in each row 101 or 102 of the SQA 100 is $1/\pi$ (where $\pi$ is the commonly understood constant, pi with a value of approximately, 3.14) and the inductance parameters in each row 101 or 102 vary over at least an order of magnitude as shown in FIG. 2 and FIG. 5. Note that a mean average for the inductance parameters of $1/\pi$ for each row 101 or 102 is more readily achieved in embodiments of the invention having twenty or even hundreds or thousands of SQUIDs in each row all biased in their linear regions despite the bias current gathering towards the ends of each row. In addition, such a mean average of $1/\pi$ for each row 101 or 102 is more readily achieved in embodiments of the invention having twenty or even hundreds or thousands of SQUIDs in each row despite unavoidable variations in the fabrication process. However, the inventors have discovered that the linearity and sensitivity further depends upon the order that the SQUIDs appear in each row 101 or 102 of the SQA 100. Returning to FIG. 1, a good order in accordance with an embodiment of the invention results in average voltage response 10, but a bad order for these same SQUIDs with the same inductance parameters results in average voltage response 20, which has a glitch 21 near the operating point that degrades linearity and decreases sensitivity to weak signals that are mixed with strong signals. The inventors have discovered that such a glitch 21 results when the SQUIDs with larger inductance parameters ($\beta_L$ approximately equal to or greater than $3/2\pi$) are adjacent to each other or within two SQUID loop elements to the ends of a row of the SQA.

In one embodiment, the respective inductance parameters of the SQUIDs in each row 101 or 102 of the SQA 100 vary in a distribution of the predetermined pattern, and the SQUIDs having larger respective inductance parameters according to the distribution are separated from each other and from ends of each of the row by at least two of the SQUIDs not having the larger respective inductance parameters. In one embodiment, the distribution is a Gaussian distribution 501 of a population density over the respective inductance parameters. In FIG. 2, the eight SQUIDs with heights, and hence depicted inductance parameters, falling within the Large range are separated from each other and from ends 103 and 104 of the row 101 by at least two of the remaining nineteen SQUIDs.

In one embodiment, the respective inductance parameters of the SQUIDs are nearly equally partitioned according to the distribution into smaller inductance parameters, the larger inductance parameters, and intermediate inductance parameters between the smaller inductance parameters and the larger inductance parameters. In FIG. 2 with twenty-seven SQUIDs, the small, intermediate, and large ranges would each include nine SQUIDs upon exactly equal partitioning, but nine SQUIDs cannot be separated from each other and the ends of the row by the remaining eighteen intermediate and small SQUIDs, so instead the Large range includes the eight SQUIDs shown in FIG. 2. The thresholds 161 and 162 are selected so that the SQUIDs are nearly equally partitioned into the Small, Intermediate, and Large ranges. The SQUIDs having the Large inductance parameters are separated from each other and from the ends of the row by at least one of the SQUIDs having the Small inductance parameters and at least one of the SQUIDs having the Intermediate inductance parameters.

In another embodiment with more SQUIDs, the respective inductance parameters of the SQUIDs are nearly equally partitioned into more than three ranges, and the SQUIDs in the largest range are separated from each other and the ends of the row by one of the SQUIDs in each of the ranges besides the largest range. As defined in the specification and claims, nearly equally partitioned means each pairing of the ranges differs by at most three SQUIDs or by at most ten percent of the combined number of SQUIDs in the pairing.

From the above description of Superconducting Quantum Interference Device (SQUID) Array (SQA) having Predetermined Pattern across Each Row, it is manifest that various techniques may be used for implementing the concepts of SQA 100 without departing from the scope of the claims. The described embodiments are to be considered in all respects as illustrative and not restrictive. The SQA 100 disclosed herein may be practiced in the absence of any element that is not specifically claimed and/or disclosed herein. It should also be understood that SQA 100 is not limited to the particular embodiments described herein, but is capable of many embodiments without departing from the scope of the claims.

We claim:

1. A superconducting quantum interference device (SQUID) array (SQA) comprising:
    at least one row, each row of said at least one row including a plurality of SQUIDs that are connected in parallel and include a plurality of junctions shared among the SQUIDs;
    wherein respective inductance parameters of the SQUIDs and respective critical currents of the junctions both vary in a predetermined pattern across the row,
    the respective inductance parameters of the SQUIDs in each row of said at least one row vary in a distribution of the predetermined pattern; and
    the SQUIDs having larger respective inductance parameters according to the distribution are separated from each other and from ends of each row of said at least one row by at least two of the SQUIDs not having the larger respective inductance parameters.

2. The SQA of claim 1, wherein the plurality SQUIDs, which is n SQUIDs, are connected in parallel and include the plurality of junctions, which is n+1 junctions, shared among the n SQUIDs, with each of the n SQUIDs including two of the n+1 junctions, and with each of the n SQUIDs, besides an outermost two of the n SQUIDs in each of said at least one row, sharing their two of the n+1 junctions with adjacent ones of the n SQUIDs.

3. The SQA of claim 2, wherein:
    the junctions are Josephson junctions, and
    the respective inductance parameters of the SQUIDs in each row of said at least one row vary over at least an order of magnitude and are given primarily by a plurality of geometric inductances around respective enclosed areas of the SQUIDs and a plurality of kinetic inductances of a layer of superconducting material surrounding the respective enclosed areas of the SQUIDs.

4. The SQA of claim 3, wherein said at least one row is a plurality of rows connected in series, each individual row of the plurality of rows including n>20 SQUIDs connected in parallel and having an average over the respective inductance parameters of the SQUIDs in the individual row equaling $1/\pi$.

5. The SQA of claim 1, wherein:
    the predetermined pattern includes the distribution, which is a Gaussian distribution of a population density over the respective inductance parameters;
    the predetermined pattern further includes a functional relation; and
    the respective critical currents of the junctions vary according to the functional relation of the predetermined pattern so that, despite a given bias current through said at least one row gathering in proportion to the functional relation towards the ends of each of said at least one row, all of the junctions operate within a linear region at the given bias current of a selected operating point.

6. The SQA of claim 1, wherein:
    the respective inductance parameters of the SQUIDs are nearly equally partitioned according to the distribution into smaller inductance parameters, the larger inductance parameters, and intermediate inductance parameters between the smaller inductance parameters and the larger inductance parameters; and
    the SQUIDs having the larger inductance parameters are separated from each other and from the ends of the row by at least one of the SQUIDs having the smaller inductance parameters and at least one of the SQUIDs having the intermediate inductance parameters.

7. The SQA of claim 6, wherein the respective critical currents of the junctions vary according to a functional relation of the predetermined pattern between the ends including a first and opposite second end of the row, with the respective critical currents having a maximum critical current near each of the first and second ends and with the respective critical currents having a minimum critical current between the maximum critical current near the first end and the maximum critical current near the second end.

8. The SQA of claim 6, wherein:
respective widths of the junctions vary across each of said at least one row for varying the respective critical currents of the junctions according to a functional relation of the predetermined pattern across the row; and
the respective widths of the junctions vary between the ends including a first and opposite second end of the row, with the respective widths having a maximum width near each of the first and second ends and with the respective widths having a minimum width between the maximum width near the first end and the maximum width near the second end.

9. The SQA of claim 1, wherein the respective critical currents of the junctions vary according to a functional relation of the predetermined pattern between a first and opposite second end of each row of the at least one row, with the respective critical currents having a maximum critical current near each of the first and second ends and with the respective critical currents having a minimum critical current between the maximum critical current near the first end and the maximum critical current near the second end.

10. The SQA of claim 9, wherein the functional relation is a power of:

$$J(x) = a \times \cos h[(bx^2)^c] \times \{0.5 + 0.5 \tan h[d(1-x)]\} \times \{0.5 + 0.5 \tan h[d(1+x)]\}$$

where $-1 \leq x \leq 1$ is a coordinate of the junctions varying across each row of said at least one row from $x=-1$ at the first end to $x=1$ at the second end, $J(x)$ is the respective critical currents of the junctions disposed at the coordinate x, and the power>0 and a, b, c, and d are empirical parameters of the functional relation.

11. The SQA of claim 10, wherein the power is 1, a=1.5542, b=2.2246, c=1.0513, and d=9.8919 so that all of the junctions operate within a linear region at a given bias current through said at least one row, despite the given bias current of a selected operating point gathering towards the first and second ends of each of said at least one row with the given bias current gathering proportional to the functional relation that is the power of the $J(x)$.

12. The SQA of claim 1, wherein respective widths of the junctions vary across each row of said at least one row for varying the respective critical currents of the junctions according to a functional relation of the predetermined pattern across the row.

13. The SQA of claim 12, wherein the respective widths of the junctions vary between a first and opposite second end of the row, with the respective widths having a maximum width near each of the first and second ends and with the respective widths having a minimum width between the maximum width near the first end and the maximum width near the second end.

14. The SQA of claim 13, wherein
the respective widths of the junctions are selected for varying the respective critical currents of the junctions according to the functional relation of the predetermined pattern between the first and second ends of the row, with the respective critical currents having a maximum critical current near each of the first and second ends and with the respective critical currents having a minimum critical current between the maximum critical current near the first end and the maximum critical current near the second end;
the functional relation is a power of:

$$J(x) = a \times \cos h[(bx^2)^c] \times \{0.5 + 0.5 \tan h[d(1-x)]\} \times \{0.5 + 0.5 \tan h[d(1+x)]\}$$

where $-1 \leq x \leq 1$ is a coordinate of the junctions varying across each of said at least one row from $x=-1$ at the first end to $x=1$ at the second end, $J(x)$ is the respective critical currents of the junctions disposed at the coordinate x, and the power>0 and a, b, c, and d are empirical parameters of the functional relation; and
the power is 1, a=1.5542, b=2.2246, c=1.0513, and d=9.8919.

15. The SQA of claim 13, wherein the respective widths of the junctions in a middle of the row form a plateau at the minimum width, and the respective widths of the junctions outside the plateau in the middle monotonically increase from the minimum width at the plateau to the maximum width near each of the first and second ends.

16. The SQA of claim 15, wherein the respective widths of the junctions outside the maximum width near the first and second ends monotonically decrease from the maximum width near the first end to an intermediate width at the first end and monotonically decrease from the maximum width near the second end to the intermediate width at the second end, the intermediate width between the minimum and maximum widths.

17. The SQA of claim 16, wherein the respective widths of the junctions outside the middle linearly increase from the minimum width of the plateau to the maximum width near each of the first and second ends, and the respective widths of the junctions outside the maximum width near the first and second ends linearly decrease from the maximum width near the first end to the intermediate width at the first end and linearly decrease from the maximum width near the second end to the intermediate width at the second end.

18. The SQA of claim 17, wherein the respective widths of the junctions are selected for varying the respective critical currents of the junctions so that, despite a given bias current through said at least one row gathering towards the first and second ends of each of said at least one row, all of the junctions operate within a linear region at the given bias current of a selected operating point.

19. The SQA of claim 18, wherein:
the respective inductance parameters of the SQUIDs in each of said at least one row vary over at least an order of magnitude in a Gaussian distribution of the predetermined pattern; and
the SQUIDs having larger inductance parameters according to the distribution are separated from each other and from the first and second ends of each of said at least one row by at least two of the SQUIDs not having the larger inductance parameters.

* * * * *